United States Patent

Dahlmann et al.

(10) Patent No.: US 7,008,561 B2
(45) Date of Patent: Mar. 7, 2006

(54) ETHER CARBOXYLIC ACIDS BASED ON ALKOXYLATED MERCAPTOBENZOTHIAZOLES AND USE OF THE SAME AS CORROSION INHIBITORS

(75) Inventors: Uwe Dahlmann, Heidelberg (DE); Michael Feustel, Koengernheim (DE); Rainer Kupfer, Hattersheim (DE)

(73) Assignee: Clariant GmbH, Frankfurt (DE)

( * ) Notice: Subject to any disclaimer, the term of this patent is extended or adjusted under 35 U.S.C. 154(b) by 243 days.

(21) Appl. No.: 10/477,477

(22) PCT Filed: Apr. 30, 2002

(86) PCT No.: PCT/EP02/04730

§ 371 (c)(1),
(2), (4) Date: Nov. 12, 2003

(87) PCT Pub. No.: WO02/092583

PCT Pub. Date: Nov. 21, 2002

(65) Prior Publication Data

US 2004/0152600 A1    Aug. 5, 2004

(30) Foreign Application Priority Data

May 12, 2001   (DE) ................. 101 23 210

(51) Int. Cl.
*C09K 3/00*    (2006.01)
*C07D 277/62*  (2006.01)

(52) U.S. Cl. ............... 252/394; 252/390; 548/169; 507/243; 507/939

(58) Field of Classification Search ............ 548/169; 252/394, 390; 507/939, 243
See application file for complete search history.

(56) References Cited

U.S. PATENT DOCUMENTS

| | | | |
|---|---|---|---|
| 2,129,709 A | 9/1938 | Schuette et al. ............ 260/151 |
| 2,205,021 A | 6/1940 | Schuette et al. ............ 260/457 |
| 2,280,792 A | 4/1942 | Bruson ....................... 260/464 |
| 2,485,330 A * | 10/1949 | Stewart et al. ............. 514/369 |
| 2,498,617 A | 2/1950 | Gluesenkamp .............. 260/306 |
| 2,518,109 A | 8/1950 | Zerbe ......................... 252/150 |
| 2,695,299 A | 11/1954 | Dazzi ......................... 260/306 |
| 2,762,786 A * | 9/1956 | Dazzi ......................... 524/83 |
| 3,174,933 A | 3/1965 | Klein et al. ................. 252/47.5 |
| 3,520,976 A * | 7/1970 | Buckman et al. ........... 514/367 |
| 4,066,398 A * | 1/1978 | Hwa ........................... 422/15 |
| 4,568,753 A * | 2/1986 | Akashi et al. .............. 548/174 |
| 4,789,673 A | 12/1988 | Donatsch et al. ........... 514/214 |
| 4,871,859 A | 10/1989 | Gupton et al. .............. 546/250 |
| 5,466,808 A | 11/1995 | Saukaitis ..................... 546/153 |
| 5,716,756 A | 2/1998 | Pawlowski et al. ......... 548/270.1 |
| 5,746,947 A * | 5/1998 | Vanderpool et al. ........ 252/394 |
| 5,874,608 A | 2/1999 | Pfirmann et al. ............ 560/8 |
| 6,117,364 A | 9/2000 | Vorderbruggen et al. ... 252/395 |
| 6,326,514 B1 | 12/2001 | Klug et al. .................. 562/583 |
| 6,372,918 B1 | 4/2002 | Feustel et al. ............... 548/349.1 |

FOREIGN PATENT DOCUMENTS

| | | |
|---|---|---|
| DE | 1119443 | 3/1965 |
| DE | 2064199 | 7/1972 |
| DE | 33 41 633 | 5/1985 |
| DE | 236 312 | 6/1986 |
| DE | 199 28 128 | 12/2001 |
| FR | 1.479.049 | 4/1967 |
| GB | 2 319 530 | 5/1998 |

OTHER PUBLICATIONS

Machine translation of FR 1.479.049.

\* cited by examiner

*Primary Examiner*—Philip C. Tucker
(74) *Attorney, Agent, or Firm*—Richard P. Silverman

(57) ABSTRACT

The present invention relates to compounds of formula (1) and the salts thereof which correspond to formula (2).

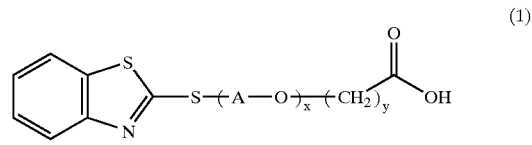

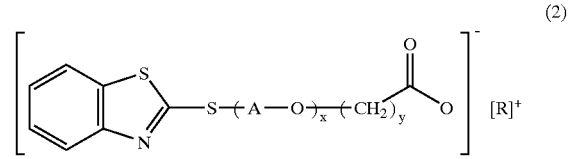

In the formulae, A is $C_2$- to $C_4$-alkylene, x is a number from 1 to 100, y is a number from 1 to 4, and R is a cation. The compound of formula (1) and/or formula (2) forms a persistent film on metal surfaces, particularly on metal surfaces under stress in metal working and in the operation of crude oil and natural gas processing.

9 Claims, No Drawings

ETHER CARBOXYLIC ACIDS BASED ON ALKOXYLATED MERCAPTOBENZOTHIAZOLES AND USE OF THE SAME AS CORROSION INHIBITORS

This application is a 371 of PCT/EP02/04730 filed Apr. 30, 2002.

The present invention relates to ether carboxilic acids from alkoxylated mercaptobenzothiazoles and to the use thereof as metal-working auxiliaries and corrosion inhibitor.

Ether carboxilic acids, i.e. organic carboxylic acids which, as well as the carboxyl function, carry one or more ether bridges, or alkali metal or amine salts thereof, are known as mild detergents with a high lime soap dispersibility. They are used in detergent formulations and cosmetics formulations, but also in technical applications (e.g. metal-working fluids, cutting fluids). These products are prepared in accordance with the prior art either by alkylation of alcohol or fatty alcohol oxyethylates or oxypropylates with chloroacetic acid derivatives (Williamson ether synthesis) or from the same starting materials by oxidation with various reagents (atmospheric oxygen, hypochlorite, chlorite) with catalysis with various catalysts.

DE-A-199 28 128 discloses a process for the preparation of ether carboxylic acids with a low residual alcohol content by reacting fatty alcohols firstly using noncatalytic amounts of alkali metal catalyst (NaOH, KOH, alkoxides above 5 mol %) with alkylene oxides, and then converting the resulting highly alkaline reaction mixtures, which consist of a mixture of oxyethylated alcohols and alkoxides of various polyalkylene glycol ethers, in a classic Williamson synthesis with sodium chloroacetate into the corresponding ether carboxilic acid. Through this, the residual content of fatty alcohol in the ether carboxilic acid is reduced without special catalysts.

GB-A-2 319 530 discloses a corrosion inhibitor for iron metals which is suitable in particular for oil recovery. This comprises a straight-chain or branched mercaptocarboxylic acid having 2 to 6 carbon atoms, and an amine substituted by carbonyl and carboxyl groups.

U.S. Pat. No. 6,117,364 discloses a corrosion inhibitor which counteracts acid corrosion on equipment in crude oil recovery. It comprises a mixture of cinnamaldehyde and organic sulfur compounds, including 2-mercaptobenzothiazole.

Mercaptobenzothiazole and various derivatives thereof, and also processes for its preparation are described in the prior art.

U.S. Pat. No. 2,498,617 discloses mercaptobenzothiazoles which have been ethoxylated with up to 30 mol of ethylene oxide. Compounds of this type are used as inhibitors in the acid pickling of iron and steel.

U.S. Pat No. 2,695,299 and U.S. Pat. No. 2,762,786 disclose compounds of the formula

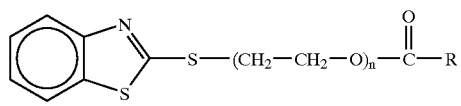

in which n is a number from 1 to 30 and R is a hydrocarbon radical. Compounds of this type are referred to as plasticizers for plastics.

The properties of substances which are used as corrosion-inhibiting media for metal-working and also for crude oil and natural gas recovery and processing depend heavily on their ability to form readily adhering films on metal surfaces. These films should be persistent even under considerable mechanical stress, such as during grinding, cutting and boring of metal work pieces and at high flow rates in natural gas/crude oil pipelines. It has been found that the ether carboxilic acids of the prior art do not demonstrate adequate film formation and persistence in all cases, and thus do not offer adequate corrosion protection.

The object was therefore to find novel substances which exhibit improved film formation and film persistence.

Surprisingly, it has been found that ether carboxylic acids from mercaptobenzothiazoles have excellent film formation and improved corrosion protection.

The invention therefore provides compounds of the formula (1)

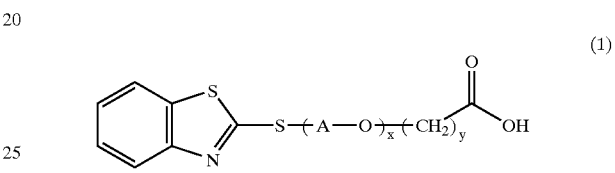

and salts thereof of the formula 2

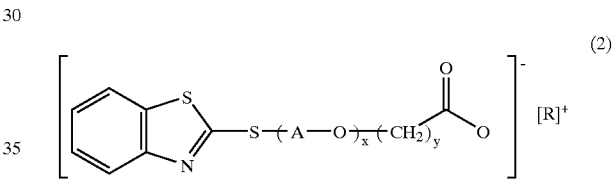

in which
A is $C_2$- to $C_4$-alkylene,
x is a number from 1 to 100, and
y is a number from 1 to 4, and
R is a cation.

The invention further provides for the use of the compounds of the formula 1 and/or 2, preferably compounds of the formula 1, as corrosion inhibitor, preferably in crude oil and natural gas recovery and processing.

The invention further provides for the use of the compounds of the formula 1 and/or 2 as metal-working medium.

A is preferably propylene or ethylene, in particular ethylene. In a further preferred embodiment of the invention, the group —$(A—O)_x$— is a mixed alkoxy group which can contain ethylene, propylene and butylene radicals. If it is a mixed alkoxy group, then the ratio of groups derived from ethylene oxide to the groups derived from propylene oxide or butylene oxide is preferably between 10:1 and 1:1.

x is preferably a number between 2 and 70, in particular 3 to 50.

y is preferably a number from 1 or 2, in particular 1.

R can be hydrogen ions in a preferred embodiment. In a further preferred embodiment, R is alkali metal or alkaline earth metal ions, in particular lithium, sodium, potassium, magnesium or calcium.

In a further preferred embodiment, the cations used are ammonium ions of the formula $NR^1R^2R^3R^4$, where $R^1$, $R^2$, $R^3$ and $R^4$, independently of one another, can be H, $C_1$- to $C_{22}$-alkyl, $C_6$- to $C_{18}$-aryl, $C_7$- to $C_{22}$-alkylaryl and/or $C_1$- to $C_{22}$-alkenyl. The radicals $R^1$, $R^2$, $R^3$ and $R^4$ can contain heteroatoms such as N, P, O, S. The ammonium radicals can be monoalkylammonium, dialkylammonium, trialkylammonium or tetraalkyl-ammonium radicals in which the alkyl substituents may, independently of one another, be occupied by up to 3 hydroxyl groups. Preferably, R is ammonium radicals which carry one, two, three or four $C_2$- to $C_{10}$-alkyl radicals. In a further preferred embodiment, one, two or three of the radicals $R^1$ to $R^4$ may be alkoxylated.

Suitable amines for the preparation of ammonium cations R are monoamines with primary or secondary amino function, such as methylamine, ethylamine, butylamine, laurylamine, coconut fatty amine, stearylamine, dimethylamine, diethylamine, dibutylamine, but also di- and polyamines, such as, for example, 3-dimethylaminopropylamine, 3-diethylaminopropylamine, 3-morpholinopropylamine, diethylenetriamine, triethylenetetramine or tetraethylenepentamine.

Suitable aminoalcohols for the preparation of ammonium cations R are, for example, N,N-dimethylaminoethanol, N,N-diethylaminoethanol, N,N-dibutylaminoethanol, 3-dimethylaminopropanol, N-hydroxyethylmorpholine, monoethanolamine, diethanolamine, triethanolamine, 3-aminopropanol, isopropanolamine, 2-(2-aminoethoxy)ethanol and cyclohexylamino-N,N-diethanol.

Suitable aminoalkylthiols for the preparation of ammonium cations R are cysteamine and cystamine.

The compounds according to the invention can be prepared by firstly alkoxylating mercaptobenzothiazole and then reacting it with monochlorocarboxylic acids. Mercaptobenzothiazole is referred to below as MBT.

MBT is generally reacted with ethylene oxide, propylene oxide, butylene oxide or mixtures of different such alkylene oxides, where ethylene oxide or mixtures of ethylene oxide and propylene oxide are preferred. Based on MBT, 1–30 mol of alkylene oxide are supplied, preferably 1–12 mol.

Suitable solvents for the alkoxylation are inert ethers, such as dioxane, tetrahydrofuran, glyme, diglyme and MPEGs. Water and also alcohols, such as propanols, butanols and oxyethylated monoalcohols, such as butyl glycol, isobutyl glycol and butyl diglycol, can be used, but lead to a high proportion of secondary products.

As basic compound for the preparation of the oxyethylated MBT it is possible to use alkaline earth metal/alkali metal hydroxides or alkoxides (sodium methoxide, sodium ethoxide, potassium tert-butoxide), but preferably alkali metal hydroxides, particularly sodium hydroxide or potassium hydroxide.

The basic compounds are used in amounts of about 5–95 mol %, based on MBT, preferably between 15 and 90 mol %, particularly preferably between 20–60 mol %.

Starting from MBT, the thiolate necessary for the oxyalkylation is prepared by reaction with the basic compounds. In order to avoid relatively high proportions of secondary products (glycols, glycol ethers of lower alcohols) in the end product, the resulting water of reaction or the corresponding lower alcohol should be removed from the reaction mixture prior to the reaction with the alkylene oxide. This can either be carried out by reacting the MBT with an alkali metal hydroxide and distilling off the water of reaction, or by reacting the base alcohol with an alkoxide of the lower alcohol and distilling off the lower alcohol. On the other hand, MBT can be monoalkoxylated in a two-stage process, in the first step without the addition of the basic compounds. In a further step, the necessary reaction to give the alkoxide then takes place.

The resulting mixture MBT and the corresponding thiolate or alkoxide is then reacted with about 1–30 mol of an alkylene oxide, preferably ethylene oxide and/or propylene oxide, the reaction temperatures here are about 80 to 160° C. A narrower homolog distribution arises during a reaction catalyzed with relatively high amounts of alkali.

In the subsequent reaction step, the MBT-oxyethylate mixture is reacted with a chlorocarboxylic acid derivative and a base, preferably dry sodium chloroacetate and sodium hydroxide. This can be carried out by reacting the oxyethylate mixture with 100 to 150 mol % of sodium chloroacetate at 30 to 100° C. and, simultaneously or subsequently, adding solid sodium hydroxide or potassium hydroxide so that the sum of the base already present in the oxyethylate mixture and the amount of base additionally added corresponds to the amount of sodium chloroacetate. The amount of base already present from the reaction with the alkylene oxide can thus be utilized directly for the subsequent Williamson synthesis and does not, as in the synthesis of a standard oxyethylate, have to be washed out.

Subsequently to the alkylation reaction, the resulting solution of the MBT ether carboxylic acid alkali metal salt can either be used directly as a compound according to the invention or converted into the free MBT ether carboxylic acid. To achieve this, the mixture is acidified with strong mineral acid (hydrochloric acid, sulfuric acid) to pH<3 and the MBT ether carboxylic acid is separated off by phase separation above its cloud point while hot as the upper phase.

The MBT ether carboxylic acid ammonium salts according to the invention are generally prepared by direct reaction of the free acid with the correspondingly functionalized amines at temperatures below 60° C.

EXAMPLES

Example 1

MBT+1EO

In a 2 l ethoxylation autoclave, 700 g of MBT were suspended in dioxane (1:1) under nitrogen blanketing and the reaction mixture was heated to 120–130° C. Then, without the addition of catalyst, ethylene oxide (EO) was injected to constant pressure and the mixture was after-reacted for 1 h at 150° C. According to the weight balance there was an EO absorption of 1 mol EO/mol of MBT. 90% of the dioxane was removed by distillation, and the intermediate product obtained was MBT+1EO in residual dioxane as a cloudy viscous liquid.

Example 2

MBT+3 EO

In a 2 l ethoxylation autoclave, 950 g of intermediate product MBT+1EO were initially introduced under nitrogen blanketing and, under NaOH catalysis (1%), gassed at 120 to 130° C. with ethylene oxide until 2 mol of EO had fully reacted with constant pressure. The mixture was after-reacted for 1 h at 150° C. Removal of readily volatile components by distillation gave the product MBT+3 EO as a pale brown viscous liquid. According to the OH number, the average EO content was 2.7.

Example 3

MBT+5 EO

In a 2 l ethoxylation autoclave, 950 g of intermediate product MBT+1 EO were initially introduced under nitrogen blanketing and, under NaOH catalysis (1%), gassed at 120 to 130° C. with ethylene oxide until 4 mol of EO had fully reacted under constant pressure. The mixture was after-reacted for 1 h at 150° C. Removal of readily volatile components by distillation gave the product MBT+5 EO as red-brown viscous liquid. According to the OH number, the average EO content was 4.9.

Example 4

MBT+3 PO+3 EO

In a 2 l ethoxylation autoclave, 700 g of MBT in dioxane (1:1) were initially introduced under nitrogen blanketing and, under NaOH catalysis (1%), gassed at 120 to 130° C. with propylene oxide (PO) until 3 mol of PO had fully reacted under constant pressure. The mixture was after-reacted for 1 h at 150° C. According to the OH number of the sample, the average PO content was 3.5 mol. Following removal of dioxane and readily volatile components by distillation, the resulting MBT+3 PO was further supplied with ethylene oxide at 120 to 130° C. until 3 mol of EO had fully reacted under constant pressure. The mixture was after-reacted for 1 h at 150° C. Renewed removal of readily volatile components by distillation gave the product MBT 3 PO+3 EO as a brown viscous liquid. According to the OH number, the average EO content was 3.0 mol.

Example 5

MBT+3 PO+7 EO

In a 2 l ethoxylation autoclave, 700 g of MBT in dioxane (1:1) were initially introduced under nitrogen blanketing and, under NaOH catalysis (1%), gassed at 120 to 130° C. with propylene oxide until 3 mol of PO had fully reacted under constant pressure. The mixture was after-reacted for 1 h at 150° C. According to the OH number of a sample, the average PO content was 3.6 mol. Following removal of dioxane and readily volatile components by distillation, the resulting MBT+3 PO was further supplied with ethylene oxide at 120 to 130° C. until 7 mol of EO had fully reacted under constant pressure. The mixture was after-reacted for 1 h at 150° C. According to the OH number of a sample, the average PO content was 3.6 mol. Following the removal of dioxane and readily volatile components by distillation, the resulting MBT+3 PO was further supplied with ethylene oxide at 120 to 130° C. until 7 mol of EO had fully reacted with constant pressure. The mixture was after-reacted for 1 h at 150° C. Renewed removal of readily volatile components by distillation gave the product MBT 3 PO+7 EO as a brown viscous liquid. According to the OH number, the average EO content was 6.9 mol.

Example 6

MBT+4 PO+7 EO

In a 2 l ethoxylation autoclave, 700 g of MBT in dioxane (1:1) were initially introduced under nitrogen blanketing and, under NaOH catalysis (1%), gassed at 120 to 130° C. with propylene oxide until 4 mol of PO had fully reacted under constant pressure. The mixture was after-reacted for 1 h at 150° C. According to the OH number of a sample, the average PO content was 4.9 mol. Following the removal of dioxane and readily volatile components by distillation, the resulting MBT+3 PO was further supplied with ethylene oxide at 120 to 130° C. until 7 mol of EO had fully reacted under constant pressure. The mixture was after-reacted for 1 h at 150° C. Renewed removal of readily volatile components by distillation gave the product MBT 3 PO+6 EO as a brown viscous liquid. According to the OH number, the average EO content was 7.2 mol.

Example 7

MBT+3 EO-ECA 572 g of MBT+3 EO (2 mol corresponding to the OH number) were initially introduced into a 2 l stirred apparatus with nitrogen blanketing and heated to 40° C. 325 g (2.4 mol) of sodium chloroacetate were then introduced and the reaction mixture was heated to 50° C. After 30 min in each case, 96 g (2.4 mol) of NaOH microprills were added in 6 portions such that the temperature does not exceed 55° C. The mixture was after-reacted for 2 h at 70° C. 900 g of 10% hydrochloric acid were then allowed to run in, the mixture was heated to 95° C. and transferred to a heatable stirrable apparatus with bottom drain outlet. Phase separation took place after 15 min at 105° C., where 1244 g of aqueous lower phase were separated off and 647 g of MBT+3 EO-ECA were obtained.

Example 8

MBT+5 EO-ECA 575 g of MBT+5 EO (1.5 mol corresponding to the OH number) were initially introduced into a 2 l stirred apparatus with nitrogen blanketing and heated to 40° C. 244 g (1.8 mol) of sodium chloroacetate were then introduced and the reaction mixture was heated to 50° C. After 30 min in each case, 72 g (1.8 mol) of NaOH microprills were added in 4 portions such that the temperature does not exceed 55° C. The mixture was after-reacted for 2 h at 70° C. 675 g of 10% hydrochloric acid were then allowed to run in, the mixture was heated to 95° C. and transferred to a heatable stirred apparatus with bottom drain outlet. Phase separation took place after 15 min at 105° C., where 909 g of aqueous lower phase were separated off and 640 g of MBT+5 EO-ECA were obtained.

Example 9

MBT+3

PO+3 EO-ECA 754 g of MBT+3 PO+3 EO (1.5 mol corresponding to the OH number) were initially introduced into a 2 l stirred apparatus under nitrogen blanketing and heated to 40° C. 244 g (1.8 mol) of sodium chloroacetate were then introduced and the reaction mixture was heated to 50° C. After 30 min in each case, 72 g (1.8 mol) of NaOH microprills were added in 4 portions such that the temperature does not exceed 55° C. The mixture was after-reacted for 2 h at 70° C. 675 g of 10% hydrochloric acid were then allowed to run in, the mixture was heated to 95° C. and transferred to a heatable stirred apparatus with bottom drain outlet. Phase separation took place after 15 min at 105° C., where 919 g of aqueous lower phase were separated off and 820 g of MBT+3 PO+3 EO-ECA were obtained.

Example 10

MBT+3 PO+7 EO-ECA 687 g of MBT+3 PO+7 EO (1 mol corresponding to the OH number) were initially introduced into a 2 l stirred apparatus under nitrogen blanketing and heated to 40° C. 163 g (1.2 mol) of sodium chloroacetate were then introduced and the reaction mixture was heated to 50° C. After 30 min in each case, 48 g (1.2 mol) of NaOH microprills were added in 4 portions so that the temperature does not exceed 55° C. The mixture was after-reacted for 2 h at 70° C. 450 g of 10% hydrochloric acid were then allowed to run in, the mixture was heated to 95° C. and transferred to a heatable stirred apparatus with bottom drain outlet. Phase separation took place after 1 h at 105° C., where 627 g of aqueous lower phase were separated off and 708 g of MBT+3 PO+7 EO-ECA were obtained.

Example 11

MBT+4 PO+7 EO-ECA 749 g of MBT+4 PO+7 EO (1 mol corresponding to the OH number) were initially introduced into a 2 l stirred apparatus with nitrogen blanketing and heated to 40° C. 163 g (1.2 mol) of sodium chloroacetate were then introduced and the reaction mixture was heated to 50° C. After 30 min in each case, 48 g (1.2 mol) of NaOH microprills were added in 4 portions such that the temperature does not exceed 55° C. The mixture was after-reacted for 2 h at 70° C. 450 g of 10% hydrochloric acid were then allowed to run in, the mixture was heated to 95° C. and transferred to a heatable stirred apparatus with bottom drain outlet. Phase separation took place after 1 h at 105° C., where 632 g of aqueous lower phase were separated off and 771 g of MBT+3 PO+7 EO-ECA were obtained.

Example 12

150 g of MBT+3 EO-ECA from example 7 were adjusted to pH 7.8 at 40° C. and with continuous stirring with 1 N NaOH with formation of the corresponding salt.

Example 13

150 g of MBT+3 EO-ECA from example 7 were adjusted to pH 10.2 at 40° C. and with continuous stirring with monoethanolamine (MEA) with formation of the corresponding ammonium salt.

Example 14

150 g of MBT+3 EO-ECA from example 7 were adjusted to pH 8.9 at 40° C. and with continuous stirring with triethanolamine (TEA) with formation of the corresponding ammonium salt.

Example 15

150 g of MBT+3 EO-ECA from example 7 were adjusted to pH 9.8 at 40° C. and with continuous stirring with 1-amino-2-propanol (MIPA) with formation of the corresponding ammonium salt.

Example 16

150 g of MBT+3 EO-ECA from example 7 were adjusted to pH 9.8 at 40° C. and with continuous stirring with cyclohexylamine with the formation of the corresponding ammonium salt.

Example 17

150 g of MBT+5 EO-ECA from example 8 were adjusted to pH 8.9 at 40° C. and with continuous stirring with triethanolamine (TEA) with formation of the corresponding ammonium salt.

Example 18

150 g of MBT+3 PO+3 EO-ECA from example 9 were adjusted to pH 8.9 at 40° C. and with continuous stirring with triethanolamine (TEA) with formation of the corresponding ammonium salt.

Use of the compounds according to the invention as corrosion inhibitor for water-miscible cutting fluids, cleaning fluids, surface treatments.

The corrosion protection test was carried out in accordance with the DIN standard 51360, part 2 (filter paper test) and is used to assess the corrosion of iron metal. A measure of the corrosion is the type and number of corrosion marks on a round filter which form as a result of the action of a cutting fluid (CF) mixed with water on standardized gray iron turnings (turning size: 3 to 6 mm$^2$). The assessment is made by means of a visual test and grading of the degree of corrosion (1 to 4) according to a comparison table.

The comparison used was commercially available emulsifiers (Emulsogen® COL 020 and COL 050).

These are essentially ether carboxylic acids of the composition oleyl-O—(EO)$_2$—CH$_2$—COOH (Emulsogen COL 020) or the homolog having 5 EO groups (Emulsogen COL 050). These were adjusted to pH 8.9 with triethanolamine (TEA) with the formation of the corresponding ammonium salt.

TABLE 1

Corrosion protection test in accordance with DIN (filter paper test), data in corrosion grades 1 to 4 according to the comparison table of DIN standard 51360, part 2 (filter paper test), concentrations in % by weight

| Example | Corrosion inhibitor/passivator | Concentration of the corrosion inhibitor/passivator | | |
|---|---|---|---|---|
| | | 2% | 3% | 4% |
| 19 (C) | Emulsogen COL 020 | — | 0–1 | 0 |
| 20 (C) | Emulsogen COL 050 | 1–2 | 0–1 | 0 |
| 21 | from example 12 | 3 | 2 | 1 |
| 22 | from example 13 | 0–1 | 0 | 0 |
| 23 | from example 14 | 2 | 0–1 | 0 |
| 24 | from example 15 | 1–2 | 0–1 | 0 |
| 25 | from example 16 | 1–2 | 0–1 | 0 |
| 26 | from example 17 | 2 | 0–1 | 0 |
| 27 | from example 18 | 2 | 0–1 | 0 |

Copper Strip Test:

The copper strip test serves as an optical assessment of the surface quality of nonferrous metals (VKIS method, worksheet 7). To pretreat the copper strips, they are heated to red-hot and quenched in methanol. The copper strip cleaned in this way is placed into a 100 ml upright cylinder which is filled with a 4% strength emulsion of the CF to be tested in demineralized water. After storage for 14 days at 50° C., the copper strips are removed from the emulsions and assessed by a visual test.

Copper Powder Test:

A 4% strength emulsion of the CF to be tested in demineralized water and exactly 1 g of copper powder are placed in a 100 ml upright cylinder. The passivator was formulated into the CF in an amount of 3%. After storage for 14 days at 50° C., the emulsions are filtered off from the copper powder and the content of $Cu^{+/2+}$ is analyzed.

For comparison, commercially available benzotriazole (Irgamet® BT) and mercaptobenzothiazolylacetic acid was used as standard passivator for copper.

TABLE 2

Copper strip test (according to VKIS) and copper powder test

| Example | Corrosion inhibitor/passivator | pH | Copper strip test | Copper powder test µg of Cu/ml |
|---|---|---|---|---|
| 28 (C) | none | 9.1 | severe discoloration | 0.44 |
| 29 (C) | Irgamet BT | 9.1 | unchanged | 0.18 |
| 30 (C) | Mercaptobenzo thiazolylacetic acid | 9.1 | unchanged | 0.43 |
| 31 | from example 7 | 9.1 | unchanged | 0.10 |
| 32 | from example 8 | 9.1 | slight discoloration | 0.11 |
| 33 | from example 9 | 9.1 | unchanged | 0.10 |

Use of the compounds according to the invention as corrosion inhibitor for exploration, production and refinery of crude oils and natural gases The corrosion inhibitors were tested in the Shell wheel test. Coupons made of C-steel (DIN 1.1203 with a surface area of 15 cm²) were dipped into a saltwater/petroleum mixture (9:1.5% strength NaCl solution adjusted to pH 3.5 with acetic acid) and exposed to this medium at 70° C. for 24 hours at a circulatory speed of 40 rpm. The concentration of the inhibitor was 50 ppm of a 40% solution of the inhibitor. The protective values were calculated from the mass decrease in the coupons, based on a blank value.

Thioglycolic acid is a compound of the formula $HS-CH_2-COOH$.

TABLE 3

(SHELL wheel test)

| Example | Corrosion inhibitor | Protection % |
|---|---|---|
| 34 (C) | Thioglycolic acid | 70–74 |
| 35 | from example 7 | 86–90 |
| 36 | from example 8 | 80–85 |
| 37 | from example 9 | 90–94 |
| 38 | from example 10 | 82–87 |
| 38 | from example 11 | 85–90 |

TABLE 4

(LPR test)

| | | Protection after [%] | | |
|---|---|---|---|---|
| Example | Corrosion inhibitor | 10 min | 30 min | 60 min |
| 39 (C) | Thioglycolic acid | 8.4 | 56.3 | 84.3 |
| 40 | from example 7 | 90.9 | 95.3 | 96.2 |
| 41 | from example 8 | 85.7 | 92.1 | 94.1 |
| 42 | from example 9 | 90.6 | 96.2 | 97.4 |
| 43 | from example 10 | 82.1 | 89.6 | 92.3 |
| 44 | from example 11 | 89.2 | 93.4 | 96.8 |

The invention claimed is:

1. A compound of the formula (1)

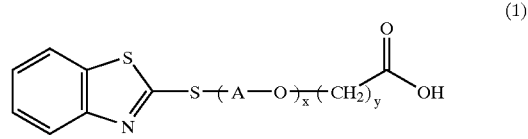

(1)

and salts thereof of the formula 2

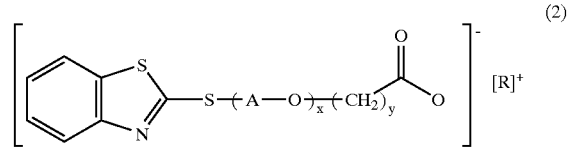

(2)

in which
A is $C_2$- to $C_4$-alkylene,
x is a number from 1 to 100, and
y is a number from 1 to 4, and
R is a cation.

2. The compound as claimed in claim 1, in which A is propylene and/or ethylene.

3. The compound of claim 1, in which x is a number between 2 and 70.

4. The compound of claim 1, in which R is a cation selected from the group consisting of hydrogen, an alkali metal ion, alkaline earth metal ion, a substituted ammonium ion, and mixtures thereof.

5. The compound of claim 1, in which y is 1 or 2.

6. A method for inhibiting corrosion of a metal comprising contacting the metal with the compound of claim 1.

7. A method for inhibiting corrosion in crude oil and natural gas recovery and processing equipment and pipelines, said method comprising forming a film of the compound of claim 1 in said equipment and pipelines.

8. A method for inhibiting the corrosion of a metal surface, said method comprising contacting the metal surface with the compound of claim 1 to provide an adhering film on said metal surface.

9. The method of claim 8, wherein the metal is subject to metal working selected from the group consisting of grinding, cutting, boring and mixtures thereof.

* * * * *